(12) United States Patent
Li et al.

(10) Patent No.: US 8,244,022 B2
(45) Date of Patent: Aug. 14, 2012

(54) METHOD FOR MEASURING DEFORMABILITY PROPERTIES OF A FIBRE

(75) Inventors: Kecheng Li, Fredericton (CA); Dongbo Yan, Vancouver (CA)

(73) Assignee: University of New Brunsick, Fredericton, New Brunswick (CA)

( * ) Notice: Subject to any disclaimer, the term of this patent is extended or adjusted under 35 U.S.C. 154(b) by 1069 days.

(21) Appl. No.: 12/116,012

(22) Filed: May 6, 2008

(65) Prior Publication Data

US 2009/0279743 A1    Nov. 12, 2009

(51) Int. Cl.
*G06K 9/00* (2006.01)
*G01B 11/00* (2006.01)

(52) U.S. Cl. .................. 382/141; 356/625; 382/111

(58) Field of Classification Search ............ 382/111, 382/141; 356/625
See application file for complete search history.

(56) References Cited

U.S. PATENT DOCUMENTS

| | | | |
|---|---|---|---|
| 4,253,329 A | 3/1981 | Karnis | |
| 5,311,290 A * | 5/1994 | Olson et al. | 356/634 |
| 5,331,405 A | 7/1994 | Fransson et al. | |
| 5,804,281 A * | 9/1998 | Phan et al. | 428/137 |
| 2002/0117274 A1 * | 8/2002 | Jang | 162/49 |
| 2005/0122514 A1 * | 6/2005 | Jang | 356/365 |
| 2010/0020168 A1 * | 1/2010 | Ye | 348/92 |

OTHER PUBLICATIONS

"Measurement of Measurement of Wet Fiber Flexibility of Mechanical Pulp Fibers by Confocal Laser Scanning Microscopy", Dongbo Yan, Kecheng Li, and Yajun Zhou, Tappi Journal, Jan. 2008, pp. 25-31.*

"Using confocal microscopy to characterize the collapse behavior of fibers," H.F. Jang and R.S. Seth, Tappi Journal, vol. 81, No. 5, May 1998, pp. 167-174.*

Dongbo, Yan; Kecheng Li, Measurement of Wet Fiber Flexibility by Confocal Laser Scanning Microscopy, Journal of Materials Science, vol. 43 No. 8, 2008, pp. 2869-2878.

Nilsson, B., Lars Wågberg and Gray, D., "Conformability of wet pulp fibres at small Length Scales". 12th Fundamental Research Symposium, p. 211 (2001).

Jang, H.F., "A theory for the transverse collapse of wood pulp fibres". 12th Fundamental Research Symposium p. 193 (2001).

Samuelsson, L.G., "Measurement of the stiffness of fibres". Svensk. Papperstidn 15(1):S41-S46 (1963).

Mohlin, U-K., "Cellulose fibre bonding Part 5: Conformability of pulp fibres". Svensk. Papperstidn 78(11):412-416 (1975).

Kerekes, R.J. and Tam Doo, P.A., "Wet fibre flexibility of some major softwood species pulped by various processes". J. Pulp Paper Sci. 11:60-61 (1985).

Kuhn, D.C.S., Lu, X., Olson, J.A. and Robertson, A.G., "Dynamic wet fibre flexibility measurement device". J. Pulp Paper Sci. 21(1):337 (1995).

Steadman, R. and Luner, P., "The effect of wet fibre flexibility of sheet apparent density". 8th Fundamental Research Symposium p. 211 (1981).

Seborg, C.O. and Simmonds, F.A., "Measurement of stiffness in bending of single fibres". Paper Trade Journal 113(1):49-50 (1941).

(Continued)

*Primary Examiner* — Wenpeng Chen
(74) *Attorney, Agent, or Firm* — Eugene F. Derényi; Fogler, Rubinoff LLP

(57) ABSTRACT

A method for measuring a property of a fiber, such as flexibility, collapsibility and moment of inertia. A fiber is wetted and deformed in its wet state, and an optical section image of the deformed fiber is taken. A measurement is made on the image and the desired property is calculated using the measurement.

10 Claims, 18 Drawing Sheets

OTHER PUBLICATIONS

James, W.L., A method for studying the stiffness and internal friction of individual fibres. Wood Sci. 6(1):30-38 (1973).

Tam Doo, P. A. and Kerekes, R.J., "Method to measure wet fibre flexibility". Tappi 64:113-116 (1981).

Zhang, M., Hubbe, M.A., Venditti, R.A. and Heitmann, J.A., "Effects of sugar addition before drying on the wet flexibility of redispersed kraft fibres". J. Pulp Paper Sci. 30:29-34 (2004).

Delgado, E., Lopez-Dellamary, F.A., Allan, G.G., Andrade, A., Contreras, H., Regla, H. and Cresson, T., "Zwitterion modification of fibres: Effect of fibre flexibility on wet strength of paper". J. Pulp Paper Sci. 30:141-144 (2004).

Karnis, A., "Mechanism of fibre development in mechanical pulping". J. Pulp Paper Sci. 20(1):280-288 (1994).

Otsu, N., "A threshold selection method from gray-level histograms". IEEE Transactions on Systems, Man and Cybernetics SMC-9:62-6 (1979).

Jang, H.F. and Seth, R.S., "Characterization of the collapse behaviour of papermaking fibres using confocal microscopy". In the proceedings of the 84th Annual Meeting of the Technical Section of Canadian Pulp and Paper Association, p. 205 (1998).

Mark, R.E., Handbook of Physical Testing of Paper II, Marcel Dekker, NY, (2002).

Jang, H.F., Robertson, A.G. and Seth, R.S., "Measuring fibre coarseness and wall thickness distributions with confocal microscopy". In the proceedings of 78th Annual Meeting of the Canadian Pulp and Paper Association, Montreal, Quebec, Canada, p. 189 (1992).

Waterhouse, J.F. and Page, D.H., "The Contribution of Transverse Shear to Wet Fibre Deformation Behavior". Nordic Pulp and Paper Research Journal 19:89-92 (2004).

Lawryshyn, Y.A. and Kuhn, D.C.S., "Large deflection analysis of wet fibre flexibility measurement techniques". J. Pulp Paper Sci, 22(1):423-431 (1996).

Lowe, R. Ragauskas, A. and Page, D.H. "Imaging fibre deformations". In Advances in Paper Science and Technology, Proc. 13th Fundamental Research Symposium (S.J. I'Anson, ed.), pp. 921, FRC, Manchester, 2005.

Ehrnrooth, E.M.L. and Kolseth, P., "The tensile testing of single wood pulp fibres in air and water". Wood Fibre Sci. 16(4):549-566 (1984).

\* cited by examiner

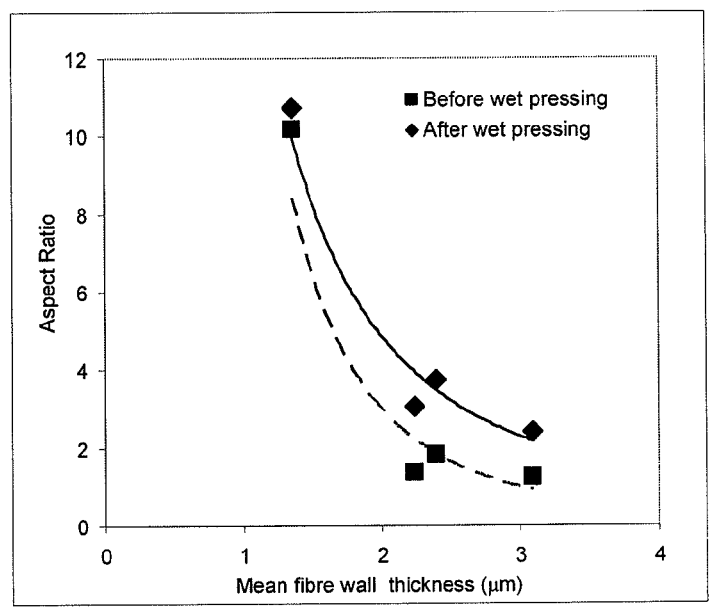
(a)
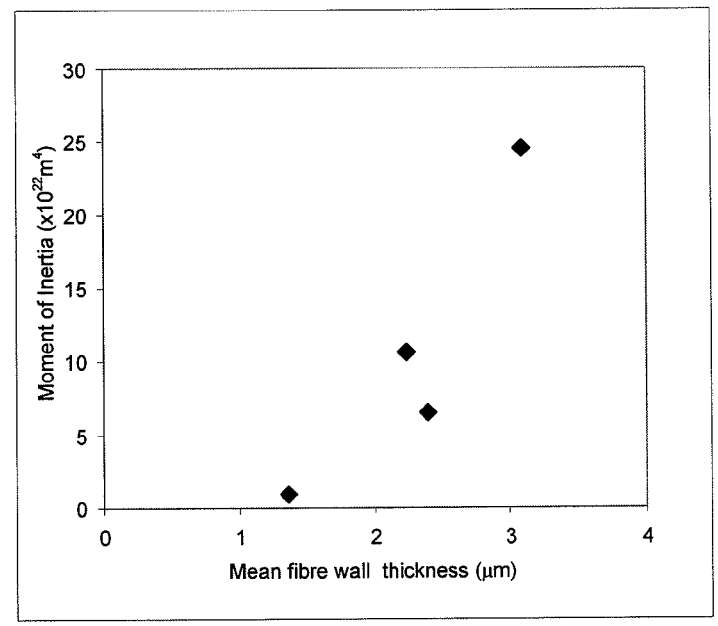
(b)
FIG. 18

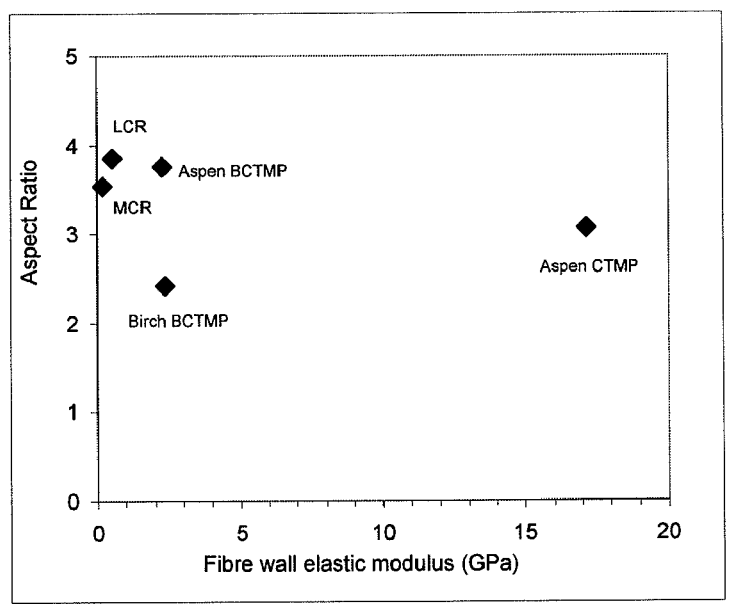
(a)
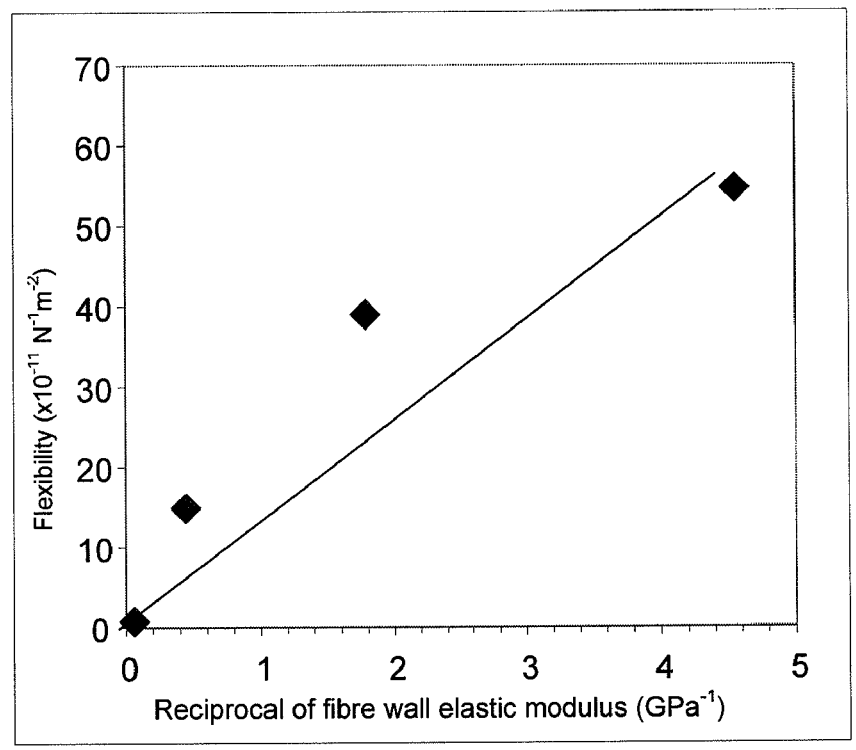
(b)
FIG. 19

| Pulp Sample Type | No. of Fibres measured | Freespan length ($\mu m$) | Support glass rod diameter (um) | Deflection ratio (%) | Flexibility ×10$^{-11}$ ($N^{-1}m^{-2}$), |
|---|---|---|---|---|---|
| Spruce BKP* | 31 | 59.3 | 12.8 | 21.6 | 73.7 |
| Aspen BCTMP | 52 | 67.8 | 12.4 | 18.3 | 14.8 |
| Aspen CTMP | 44 | 160.1 | 12.1 | 7.6 | 0.7 |
| Birch CTMP | 74 | 192.5 | 12.8 | 6.7 | 0.8 |
| Birch BCTMP | 40 | 128.9 | 15.3 | 11.9 | 2.9 |
| LCR | 42 | 51.9 | 10.0 | 19.2 | 39.0 |
| MCR | 52 | 43.6 | 9.8 | 22.4 | 54.7 |

*Pressed at 220kPa

FIG. 22

| Fibre Type | Mean Fibre thickness (μm) | Median value of Freespan length at neutral bending plane (μm±SD) | Measured freespan length with LM (μm±SD) | Relative difference of measured freespan length between CLSM and LM |
|---|---|---|---|---|
| Aspen CTMP | 7.6±1.9 | 160.1±61.6 | 103.1±61.0 | -35.6 % |
| Birch BCTMP | 10.4±3.8 | 128.9±41.4 | 86.6±56.8 | -32.9 % |
| Aspen BCTMP | 6.7±1.9 | 65.3±24.1 | 65.7±29.7 | 0.6 % |
| Spruce BKP | 3.8±1.5 | 38.5±14.6 | 45.0±17.2 | 16.8 % |

SD: Standard deviation.

LM: freespan length was measured with Leica DM4500 light microscope and LCS software (Leica) under incidental light mode. 20X lens.

Simple size: 15

FIG. 23

| Pulp Sample Type | Fibre wall thickness (μm) | Aspect Ratio of un-pressed fibres | Aspect Ratio of fibres pressed at 340kPa | Moment of inertia of compressed fibres, I ×10²² m⁴ | Elastic modulus E ** (GPa) |
|---|---|---|---|---|---|
| Spruce BKP* | 1.4±0.4 | 10.2±3.3 | 10.7±3.5 | 1.0 | 1.4 |
| Aspen BCTMP | 2.4±0.5 | 1.8±0.5 | 3.8±0.9 | 6.5 | 2.3 |
| Aspen CTMP | 2.2±0.6 | 1.4±0.3 | 3.1±0.5 | 10.7 | 17.2 |
| Birch CTMP |  |  | 2.4±0.8 | 24.5 | 2.5 |
| Birch BCTMP | 3.1±0.8 | 1.3±0.3 | 2.4±0.8 | 24.5 | 2.4 |
| LCR | - | - | 3.9±1.1 | 7.5 | 0.7 |
| MCR | - | - | 3.5±0.7 | 6.6 | 0.2 |

\* Pressed at 220kPa

\*\* E was calculated from the flexibility (F) and moment of inertia (I) according to Eq. (3)

FIG. 24

METHOD FOR MEASURING DEFORMABILITY PROPERTIES OF A FIBRE

CROSS-REFERENCE TO RELATED APPLICATIONS

This is the first application filed for the present invention.

MICROFICHE APPENDIX

Not applicable

TECHNICAL FIELD

The present application relates to measuring fibre deformability in general, and to measuring the flexibility, collapsibility, and moment of inertia of fibres in particular.

BACKGROUND OF THE INVENTION

Modern paper and paper board is predominantly composed of a matrix of wood fibres. During the consolidation stage of papermaking, individual wet fibres are drawn and entangled together forming a web structure. The deformability of the wet fibres used is a significant measure of the ability of the fibres to conform to each other by providing bonding contact in the course of dewatering, pressing, and drying. Fibre flexibility is a significant measure of fibre deformability. Fibres which are flexible are more conformable to one another, thus forming more contact area among fibres.

Fibre flexibility determines the total inter-fibre contact area and the voids in the fibre network, and plays a dominant role in determining most paper properties, such as bulk, permeability, opacity, surface smoothness, and physical strength.

The fibre flexibility of mechanical pulp, such as bleached chemi-thermomechanical pulp (BCTMP) fibres, is more important when BCTMP fibres are used in wood-free fine paper grades to improve paper bulk and opacity [1].

Compared with chemical pulp fibres, which usually collapse completely during fibre processing, mechanical pulp fibres do not collapse, or collapse only partially depending on the papermaking process [2]. Collapsed fibres have higher flexibility than uncollapsed fibres, so it is important to understand how fibre collapsibility affects the fibre flexibility.

Among all properties of wood fibres, the elastic modulus of the fibre is recognized as one of the most fundamental fibre properties that affects almost all paper qualities and papermaking properties, such as sheet density, physical strength, light scattering ability, smoothness, and permeability. It is the controlling factor that determines the deformability of the fibre wall.

There are several prior art methods for measuring the flexibility of individual wet fibres.

The measurement of single fibre elastic modulus is usually performed by micro-tensile testing. The difficulties associated with this test are the dimensions of individual wood fibres, which are short (1-5 mm) and thin (10-30 um in diameter) and require careful handling and mounting techniques in sample preparation, and accurate measurements for stress and strain in a very small scale. Because of the heterogeneous nature, a large population of fibres needs to be tested for the statistical analysis. Tedious and time-consuming operations in the fibre scale become a major drawback of this test method and make it impractical for engineering applications.

Some existing prior art methods treat the fibre as a cantilever [3-7]. Most of these methods are based on small deflection beam theory, which involves measuring the displacement of a fibre beam when applying a transverse force or bending moment on the fibre. If the fibre is treated as a beam subject to pure elastic deformation, the flexibility (F) of individual fibres can be defined as the reciprocal of its bending (also sometimes referred to as flexural stiffness) EI, where E is the elastic modulus of the fibre wall and I is the moment of inertia of the fibre cross-section: $F=1/EI$.

Seborg and Simmonds [8], for example, measured the stiffness of dry fibres by clamping individual fibres into place and then exerting a force on a fibre using a quartz spring to bend it like a cantilever beam. The flexural stiffness EI is determined from the slope of the load-deflection curve. The test suffers from two main disadvantages: (1) it is done on single fibres, making it very tedious and cumbersome; and (2) the clamping can damage the fibre.

James [9] calculated the fibre stiffness by measuring the resonance frequency of a fibre cantilever. Hydrodynamic or bending beam methods have also been developed for the fibre flexibility measurement by hydrodynamic forces generated by water flow and image analysis, so that individual fibre handling can be avoided.

Various methods have been developed for supporting the fibres. For example, Samuelsson [3] used a mechanical jaw to clamp fibres. Tam Doo and Kerekes [10] supported fibre on one end of a capillary tube so that mechanical damage to the fibre can be avoided. Like the Seborg and Simmonds method, the Tam Doo and Kerekes method is limited to testing individual fibres.

Kuhn et al. [6] developed a device that bends fibres by a T-junction tube when fibres in water flow out of a capillary. The fibre deformation is observed by a microscope and the force is calculated according to hydrodynamic theory. The Kuhn method is a direct measure of the flexibility of a fibre and may give flexibility results that are higher than expected [6].

Conformability testing as opposed to directly measuring flexibility is another typical method for fibre flexibility measurement. This method was first proposed by Mohlin [4]. In this method, a fibre is wet pressed onto a thin glass fibre (diameter=60 mm) that is fixed on a glass slide. The wet fibre arcs over the glass fibre and then is allowed to dry. The non-contact span, or freespan, length of the fibre is determined to calculate the fibre flexibility according to the beam deflection theory. Since only a conventional light microscope is required, and it can provide a numerical measure in an engineering unit, this method has commonly been used for fibre flexibility measurement [11-13]. No pressure, however, is applied to the fibre when taking the measurement and most likely does not approximate what happens in a paper structure of such fibres.

Steadman and Luner [7] have sought to improve upon the Mohlin method. In the Steadman method, the stiffness (flexibility) of individual wet fibres is determined from the elastic modulus (E) and the moment of inertia (I) of the fibre wall. This method is advantageous because it does not need to handle individual fibres. In the Steadman method, a wire of 25 μm diameter was used as the support wire for forming the fibre arc over it. A larger wire will lead to a larger arc, which will be easier to identify with a conventional microscope, but a large wire will also increase the deflection ratio.

In the Steadman method, fibres are wetted and pressed onto a thin support wire that is fixed on a glass slide. The fibre and the support wire are approximately 90 degrees to one another such that when pressed onto the wire, the fibre forms an arch-like span over the wire as it deforms. The fibre is then allowed to dry and the sections of the fibre in contact with the slide become adhered to the glass slide. The length of the section of the span not in contact with the glass slide, referred to as the non-contact span or freespan length, is measured from above using a conventional light microscope with incident lights, under which the optical contact zone of the fibre and the glass slide appears in dark, whereas the non-contact zone appears in light, thus the freespan length is measured. The freespan length measurement is then used in the calculation of flexibility according to the following formula:

$$F=1/EI=72d/PWS^4$$

Where E=modulus of elasticity ($Nm^{-2}$)
I=moment of inertia ($m^4$)
d=wire diameter (m)
P=pressing pressure ($Nm^{-2}$)
W=projected fibre width (m)
S=mathematical estimate of the loaded span (m)

The fibre at which the distance between fibre surface and the glass slide is less than half of the wavelength of the light (usually assumed as 550 nm) appears in dark even if they are not contacted physically due to light interference; therefore, the freespan length is usually under-measured. Since the fibre thickness is not uniform and a fibre does not collapse uniformly along the fibre length, the thickness of the fibre cross-section affects the freespan length used for the stiffness calculation, which is neglected in this method as the conventional light microscope only generates images from the top view.

Since the moment of inertia of a fibre cross-section cannot be measured using a conventional light microscope (LM), the Steadman method has only been used for measuring fibre flexibility but not for measuring the elastic modulus. The elastic modulus can be solved only if the moment of inertia of the fibre is known but prior art methods do not yield the moment of inertia.

As discussed above, in the Steadman method, a LM is employed to observe pulp fibres. In recent years, confocal laser scanning microscopes (CLSM) have been used in pulp and paper research as an alternative to LMs for imaging fibres. However, CLSMs have not been used to take optical sections of fibres. Even where CLSMs have been used to image fibre cross-sections, the images have been of the cross-sectional surfaces of fibres which have been physically cut into cross-sections.

SUMMARY OF THE INVENTION

According to one aspect of the present invention, there is provided a method for measuring a property of a fibre which involves providing a fibre, wetting the fibre, deforming the fibre in its wet state, acquiring an optical section image of the deformed fibre, making a measurement on the image, and calculating the property using the measurement.

BRIEF DESCRIPTION OF THE DRAWINGS

FIG. 18(a) is a graph according to the invention showing the effect of fibre wall thickness on fibre collapsibility;

FIG. 18(b) is a graph according to the invention showing the effect of fibre wall thickness on moment of inertia;

FIG. 19(a) is a graph according to the invention showing the effect of fibre wall elastic modulus on fibre collapsibility;

FIG. 19(b) is a graph according to the invention showing the effect of fibre wall elastic modulus on flexibility;

FIG. 22 is a table according to the invention showing median values of flexibility of fibres;

FIG. 23 is a table according to the invention comparing freespan length and deflection height measurement; and FIG. 24 is a table according to the invention comparing fibre collapsibility and fibre-wall elastic modulii.

DETAILED DESCRIPTION OF THE INVENTION

According to one embodiment, the present invention relates to a method of taking optical sections of wet pulp fibre in order to directly observe the shape and the cross-sectional geometry of the wet fibres once they have been deformed by a pressing pressure. Measurements of various dimensions of the fibres are made using the optical section images and used for calculating the flexibility, collapsibility, moment of inertia, and in turn, the elastic modulus of the fibre wall. The elastic modulus of wood fibres is also important for the production and application of wood fibre in composite materials as a reinforced component.

Figure 1:
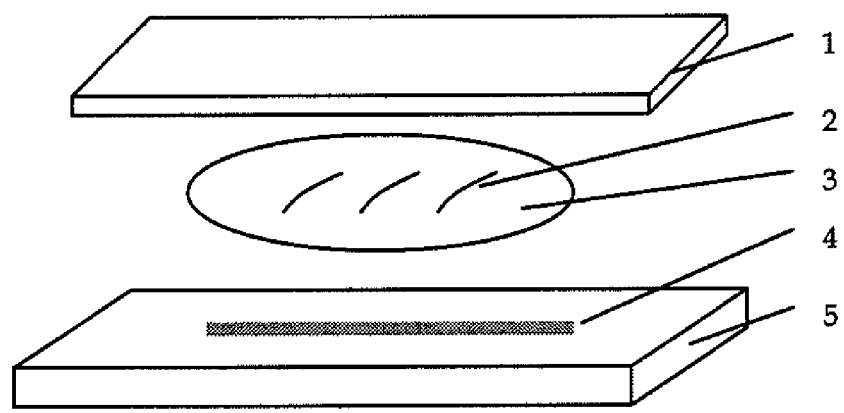
FIG. 1 is a schematic of fibres being prepared for mounting on a glass slide according to the present invention.
Figure 2:
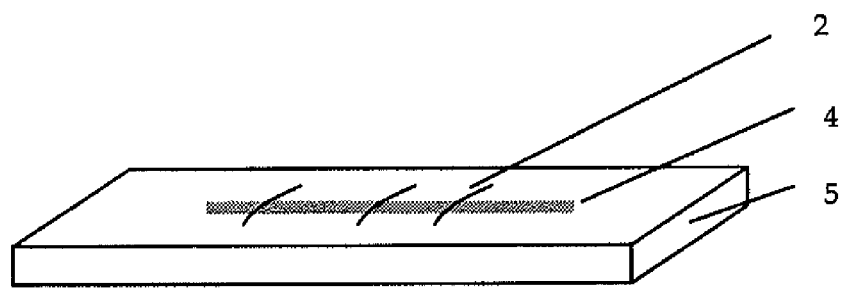
FIG. 2 is a schematic of fibres on a glass slide according to the present invention.

Referring to FIG. 1, in one embodiment of the present invention, fibres are prepared for observation in a manner similar to the set-up method using in the Steadman method. A glass fibre 4 with a diameter of about 10 um is fixed on a microscope glass slide 5. The glass fibre 4 serves as the support for the fibres 2 in the same way as the support wire in the Steadman method. Pulp fibres 2 are stained with a proper fluorescent dye and suspended in water. The fibre suspension (not shown) is swirled and then drained through a filter paper 3 and the pulp fibres 2 are deposited on the filter paper 3. The pulp fibres 2 are then wet pressed onto the glass fibre 4 and the glass slide 5 together with blotting paper 1 at a controlled pressure (P) and for a period of time, sufficient for the pulp fibres 2 to adhere to the glass slide 5. Referring to FIG. 2, when the filter paper 1 is removed, at least some of the fibres 2 should be positioned spanning the glass fibre 4 at a substantially perpendicular angle to the glass fibre 4.

Figure 3:
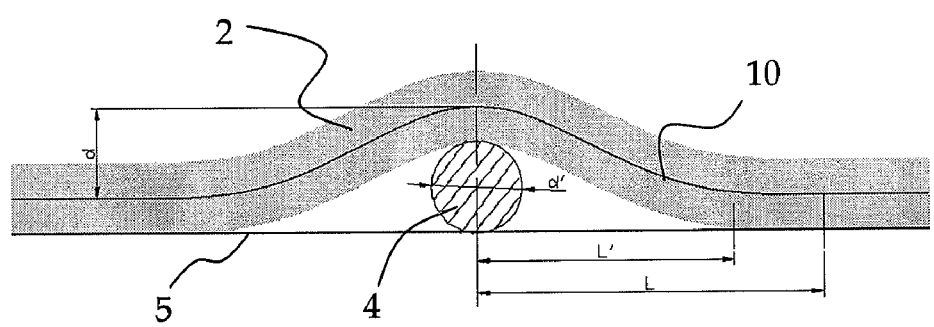
FIG. 3 is a schematic cross-section of a fibre deformed on a glass fibre according to the present invention.

FIG. 3 shows a cross-section of the glass fibre 4 with a pulp fibre 2 spanning the glass fibre 4.

Figure 4:
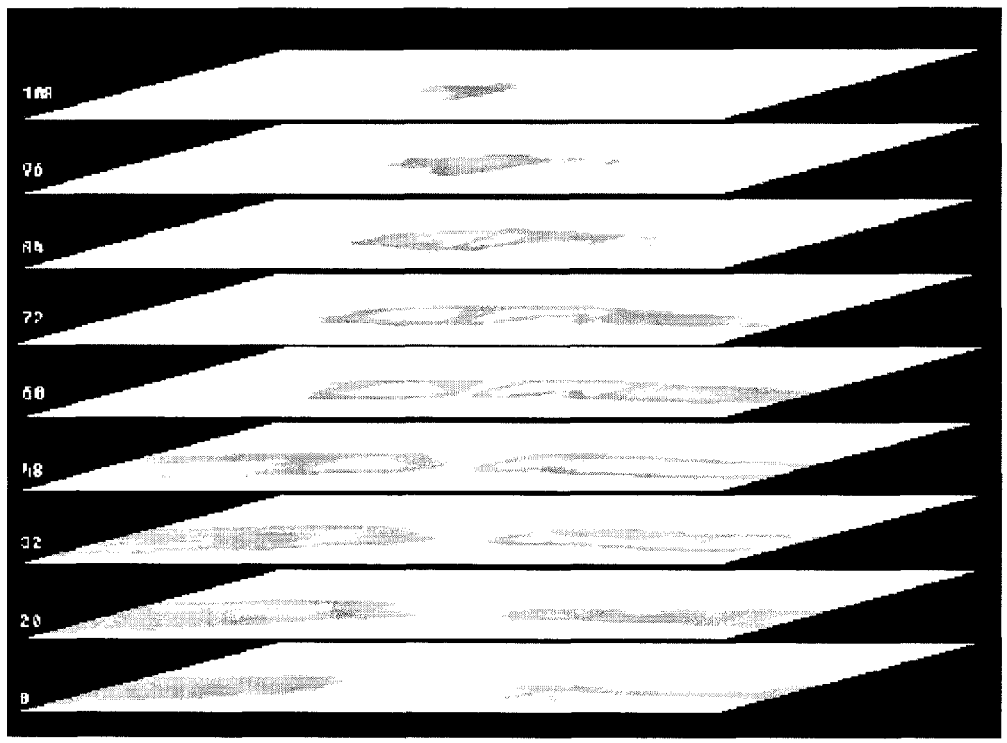
FIG. 4 is a series of images of optical sections of a fibre taken in the x-y plane according to the present invention.
Figure 5:
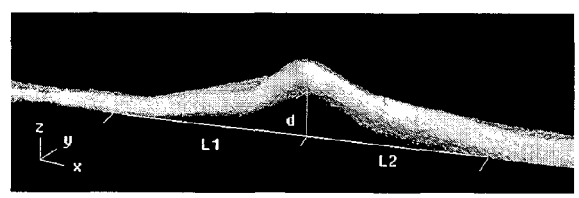
FIG. 5 is a 3D image of a fibre reconstructed from the images of FIG. 4.

A CLSM is then used to image the fibres 2. The basic imaging mode of CLSM is an XY plane or section of the sample of the focal plane. The major difference between CLSM and conventional LM is that CLSM allows only the signals from the focal plane to be recorded, so the image formed is only a plane, not the entire sample object, while in LM, signals from above and below the focal plane can be recorded. Therefore, the CLSM image is crisper and is of higher resolution. By changing the focal plane along the height direction, a series of focal planes, also called optical sections, can be imaged as shown in FIG. 4. With suitable image processing software, these optical sections can be stacked up to construct a 3D image of the object, in this case a fibre 2 as shown in FIG. 5. The glass fibre 4 is not shown in FIG. 5.

For fibre flexibility measurements, the freespan length (L) and the deflection height (d) are measured. The freespan length is the length along the x-axis of the non-contact section of the fibre span i.e. the section not in contact with the glass slide. The freespan length is L1+L2 in FIG. 5.

The deflection height d is measured in the z-axis as described in more detail below.

In order to measure the freespan length and the deflection angle, the CLSM is used to take an optical section (also referred to as a single line scan) of the fibre in the XZ plane. From the XZ plane, the transverse view of the fibre deformation can be obtained, which provides the same information as the 3D image, and from the YZ plane, the cross-sectional view of the fibre can be obtained, which can be used to determine the collapsibility of the fibre and to determine the moment of inertia of the fibre wall.

Figure 6:
FIG. 6 is a transverse optical section according to the invention of a fibre in the XZ plane.
Figure 7:
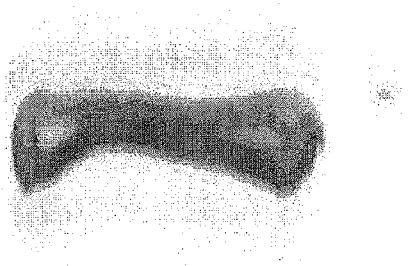
FIG. 7 is a cross-sectional optical section according to the invention of a fibre taken in the YZ plane.

An example of a transverse optical section of a fibre 2 in the XZ plane is shown in FIG. 6. An example of a cross-sectional optical section in the YZ plane is shown in FIG. 7. As described in more detail below, binary images of these optical sections are generated from which measurements can be made.

Materials and Sample Preparation

The method according to one embodiment of the invention is now described with reference to the analysis of four commercial pulps: bleached Spruce kraft pulp (BKP), Aspen CTMP, Aspen BCTMP and Birch BCTMP, obtained from two Canadian paper mills. Aspen CTMP and Aspen BCTMP are taken from the same production line. The Aspen BCTMP were further refined by a PFI mill at 4% consistency to 3000 revolutions and at 10% consistency to 4000 revolutions, denoted as LCR and MCR, respectively. The Canadian Standard Freeness (CSF) of LCR and MCR are 236 mL and 268 mL, respectively.

Acetone washed glass fibres were deposited on glass microscope slides (Fisher brand precleaned microscope slide) as support wires for the pulp fibres prior to depositing pulp fibres on them. Glass fibres (0.5 g, CDS Analytical 1001-0345) are suspended in 1 L of distilled water and drained onto a piece of filter paper (Fisher brand Q8) by a TAPPI standard handsheet former. The suspension was swirled before draining so that it was spinning while draining down, thus glass fibres became oriented approximately in parallel close to the edge of the filter paper. Then the glass fibres were transferred onto the microscope slides by placing and gently tapping the filter paper onto the slides.

To enhance the fluorescence intensity, pulp fibres (0.3 g o.d) were stained in 20 ml 0.1% Safranin-O for 24 hours at room temperature, and then diluted to 0.03% consistency and drained onto a filter paper in the same manner as was done for the glass fibres. The filter paper with fibres was placed on two pieces of dry blotting paper, and then pressed onto eight glass microscope slides at 340 kPa by a standard handsheet press (Labtech) for 5 minutes. Prior to pressing, the glass slide and the filter paper were arranged in a way so that the pulp fibres and the glass fibres cross each other perpendicularly. The actual pressures on fibre samples are calculated based on the projected fibre area. Slides are dried in air and kept under TAPPI standard conditions before CLSM imaging. It should be noted that not all the fibres cross each other perpendicularly. A pulp fibre was measured only when it crossed a glass fibre at a perpendicular angle, i.e., 90 degrees±10 degrees. About 30% to 50% of fibres form almost perpendicular crossings. Since there are about a thousand pulp fibres on a single glass slide, sufficient perfect crossings can be found for the measurements to be carried out.

CLSM Operation

Image scanning was carried out with a Leica TCS-SP2 confocal laser scanning microscope. A dry objective lens (HC FLOUTAR 50×) with a numerical aperture of 0.8 is used for imaging transverse and cross-section of fibres that were wet pressed on a glass slide. An excitation wavelength of 514 nm from an Ar laser is used. The pinhole size is set at the optimum value by Leica Confocal Control software. The emission light collected by detector (PMT) is set from 525 nm to 760 nm. The gain and offset of PMT are automatically adjusted for each fibre by software to ensure a constant image quality. The CLSM is operated in XZ scanning mode to obtain both a transverse and a cross-sectional image. Scanning step size in Z direction is 0.12 um. An oil immersion lens (HCX OLAPO CS 63×1.4) was used for imaging fibre cross-section before wet pressing.

Image Processing

Figure 8:
FIG. 8 is a binarized image of the fibre of FIG. 6.

To improve the accuracy of the measurement and avoid subjective errors, image processing is performed with the image processing toolbox in Matlab 7.0 (Mathworks Inc.). CLSM images are smoothed using lowpass filtering and then converted into binary format (see FIGS. 8, 9 and 10). The threshold for binarization was determined automatically by the double peak histogram method [14, 15]. All measurements were carried out on the binarized images.

Freespan Length (L) and Deflection Height (d)

Figure 9:
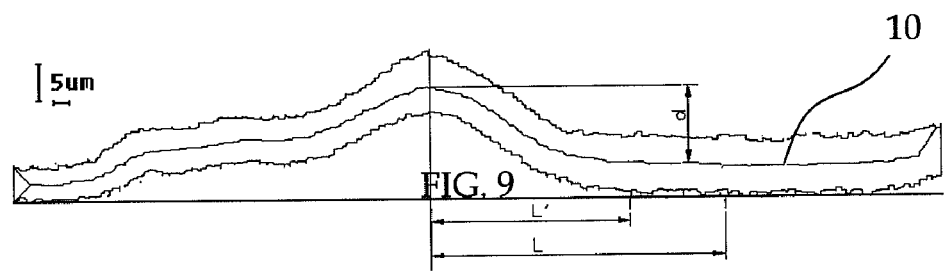
FIG. 9 is a skeletonised image of the fibre of FIG. 8 with a neutral bending plane.

Since the fibre thickness is not uniform along the fibre length and a fibre does not collapse uniformly along the fibre length, the thickness of the fibre cross-section may affect the deflection height and freespan length. In this example, a neutral bending plane 10 is defined as the symmetric centre in fibre thickness along the fibre length (see FIG. 9). The neutral bending plane 10 is located by applying a skeletonization operation to the fibre transverse images [16]. Since fibre edges on the binarized image are usually not smooth, several "open" operations are required before skeletonization so that the object can be smoothed and isolated pixels removed. The deflection height (d) is defined as the vertical distance between the highest and the lowest pixels on the neutral bending plane. The freespan length is defined as the horizontal distance between the highest pixel and the lowest pixel at the start point of the horizontal segment of the neutral bending plane. In FIG. 9, the freespan length as measured by a conventional LM is indicated by L', and the freespan length as measured by a CLSM according to the method the invention is indicated by L.

Fibre Collapsibility (AR) and Moment of Inertia (I)

Figure 10:
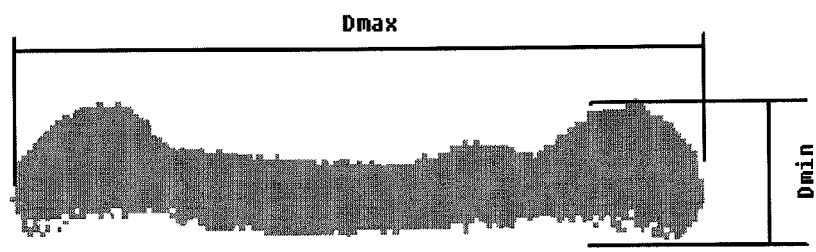
FIG. 10 is a binarized image according to the invention of a collapsed fibre taken in the YZ plane.

With reference to FIG. 10, fibre collapsibility was measured as the aspect ratio of the fibre cross-section dimension in Eq. 1 according to Jang [17]:

$$AR = \frac{D_{min}}{D_{max}} \quad (1)$$

where $D_{min}$ is the fibre thickness (shortest Feret diameter) and $D_{max}$ is the fibre width (longest Feret diameter), which were obtained from a binarized fibre cross-sectional image. The cross-sectional images were taken from the fibre on the top of the glass fibre 4 (support wire). The main reason that this portion of the fibre was chosen for collapsibility measurement is that this portion of the fibre was subjected to the maximal stress, and it is consistent if the same spot was chosen for all the fibres measured throughout the example. In an alternate embodiment, the cross-section could be extracted from part of the freespan region, but not the part which is in contact with the glass slide since the part in contact with the glass slide may not contribute much to the deformation process of the fibre under stress.

Figure 11:
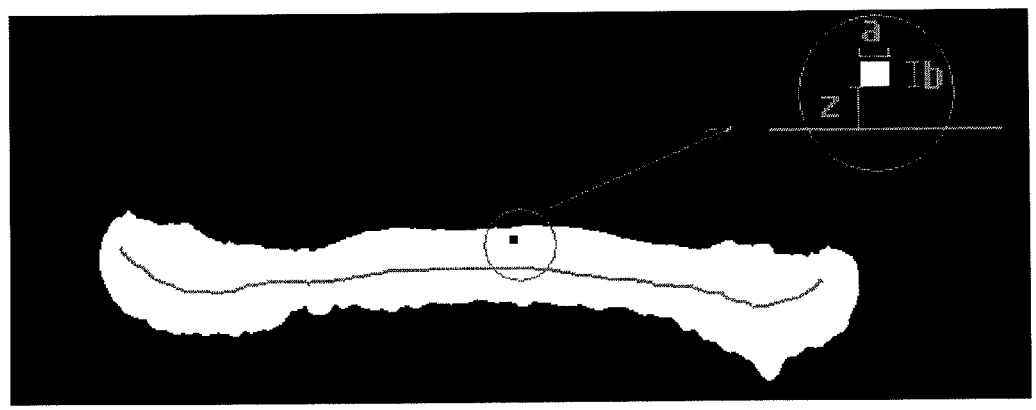
FIG. 11 is a binarized image of an optical section according to the invention of a fibre taken in the YZ plane.

With reference to FIG. 11, because of the irregular shape of the fibre cross-section, the moment of inertia (I) of fibre with regard to the neutral bending plane was calculated based on the relative location of each pixel (Eq. 2) [18].

$$I = \sum I_i = \sum \left( \frac{ab^3}{12} + A_i z^2 \right) \quad (2)$$

where a and b are the width and height of the pixel, respectively, A is the area of a pixel and z is the distance of pixel i to the neutral bending plane. The fibre wall thickness was only measured on the fibres without wet pressing from the fibre cross-sectional images following Jang's procedure [14, 19].

Figure 12:
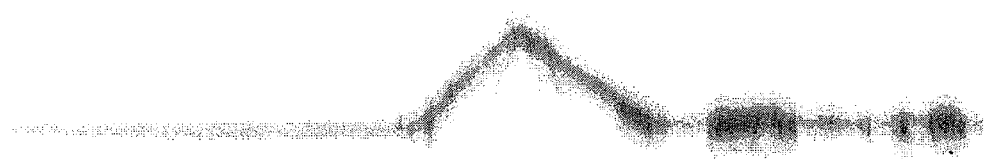
FIG. 12 is an optical section according to the invention of a wet bleached kraft pulp (BKP) fibre taken in the XZ plane.

Typical images of the transverse view of the fibre deformation acquired with CLSM XZ scanning mode are shown in FIG. 12. From these images, fibre deformation height and freespan length are measured. Fibre flexibility was calculated based on the Steadman method by assuming that the fibres are subjected to only pure bending (Eq. 3):

$$\text{Flexibility} = \frac{1}{EI} = \frac{72d}{qL^4} \quad (3)$$

where E and I are the elastic modulus and the moment of inertia of the fibre wall, respectively, d is the deflection height, L is the freespan length and q is the pressing load on the fibre in N/m.

Figure 13:
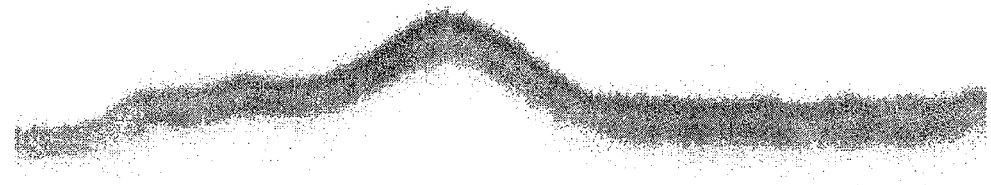
FIG. 13 is an optical section according to the invention of a wet BCTMP fibre taken in the XZ plane.

It was observed that almost all BKP fibres were collapsed and solid fibre walls were imaged (FIG. 12). In comparison, mechanical pulp fibres were not completely collapsed, which can be seen from the lumen area appearing dark between the fibre walls (FIG. 13). The shapes of the deformation of the two types of fibres were also distinguishable. The shape of the deformation of the BKP fibres appeared straight, resembling a shear deformation, but that of the BCTMP appeared more like a bending deformation. This confirms Waterhouse and Page's finding [20] that shear contribution can be substantial in the Steadman and Luner method. In this embodiment, only bending deformation is considered based on the Steadman and Luner method. To limit the shear contribution and make the results comparable to other hardwood pulp fibres, the pressure used for BKP fibres was reduced to 220 kPa, and the resultant deflection ratio of it was about 20%, close to that of hardwood pulp samples.

Figure 14:
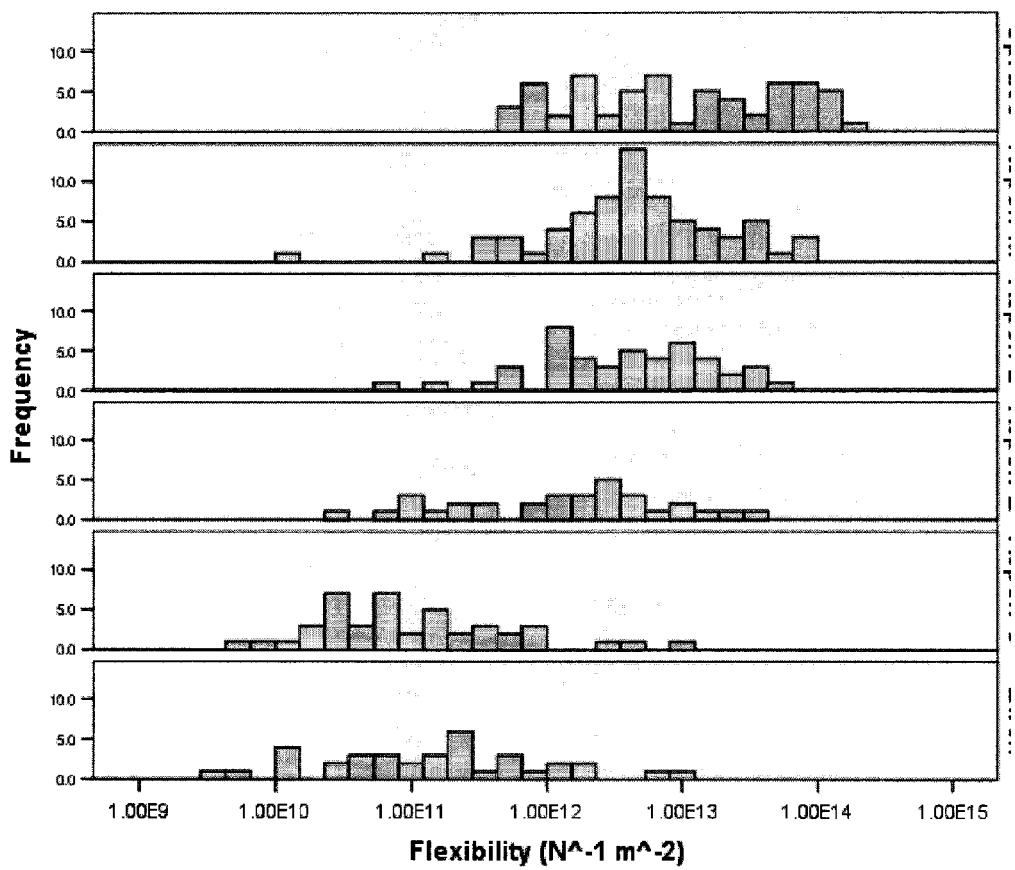
FIG. 14 are bar graphs of distribution of measured flexibility according to the present invention.

Various types of pulp fibres were measured using the method. About 40-50 fibres of each pulp sample were measured. It can be seen from FIG. 22 that the deflection ratios, which are the ratios of the deflections in fibre thickness direction to the freespan lengths, are about 20% or below. According to Lawryshyn and Kuhn [21], when the small deflection theory is used, as in the Steadman method, the error introduced can be controlled to about 5% when the deflection ration is less than 20%. Due to the heterogeneity of pulp fibres, the flexibility values of each pulp distribute in a wide range (FIG. 14). Therefore, the median value of flexibility for each sample is presented in FIG. 22. The measured flexibility values of each pulp sample were also compared using analysis of variance test (One-way ANOVA) with SPSS (SPSS Inc., USA). The significance between any two samples is less than 0.001, which indicates that this method is able to differentiate different types of fibres effectively with a sample size of about 50.

Freespan Length by CLSM and LM

One advantage of using CLSM is that CLSM can accurately identify the physical contact points from the transverse view of the fibre span, and hence the exact freespan length can be measured. With introducing the concept of "neutral bending plane" as discussed foregoing, the accuracy of the freespan length measured is even greater. Another advantage is that the deflection height can be measured directly other than being assumed to be the diameter of the support wire. As reported by Lowe et al. [22], in some cases the overlaying fibre may conform to the support fibre by overlapping. FIG. 9 illustrates the difference in measured freespan length by a CLSM and a light microscope (LM) for a perfect span shape. Due to light interference between the glass slide and the fibre, LM is only able to identify the optical contact points so the measured freespan length is "L'" measured with a LM in comparison with "L" measured with a CLSM.

Figure 15:
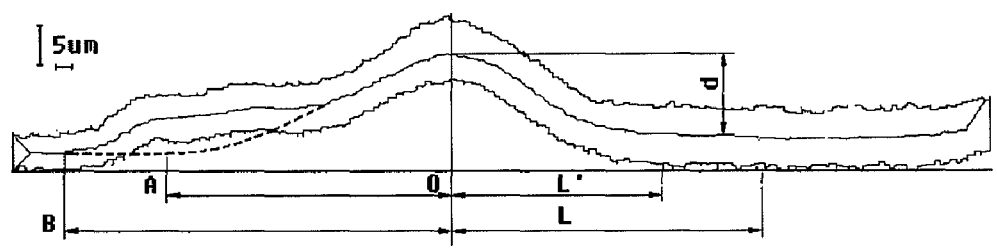
FIG. 15 is a schematic cross-section of a fibre non-symmetrically deformed on a glass fibre according to the present invention.

FIG. 23 shows the difference in the average freespan length measured with CLSM and LM (Leica DM4500 microscope). For thick-walled and partially collapsed fibres (BCTMP and CTMP), the freespan measured by a CLSM (L) is up to 35% larger. However, for flexible and thin-walled fibres, the freespan measured with a LM is greater than that measured with a CLSM. According to the illustration in FIG. 9, L is always larger than L', but this is only for a perfect deformation shape. In reality fibres do not always deform like that, and the deformation is not symmetrical about the central point or the support wire. This is probably due to the non-uniformity of fibre wall structure. With CLSM, only the perfect deformation on the right side is measured since the shape can be seen. With LM, the freespan lengths of both sides are measured without seeing the deformation shape. In some cases, as shown in FIG. 15, the first contact point (A) can be missed due to irregular deformation shape and the second contact point (B) is taken as the contact point, thus, the left half OB is much larger than the real freespan OA. It was observed in this example that about 50% BCTMP fibres formed irregular deformation; only perfect span shape was measured for calculating the fibre flexibility. The rationale behind this is that if irregular deformation is formed, that means the operation or the result does not comply with the beam deflection theory, so the measurement or calculation would be invalid. This is another benefit of using CLSM. A light microscope cannot identify the irregular shape so all kinds of deformation were measured which lead to errors in the measurements.

Fibre Collapsibility and Moment of Inertia

Figure 16:
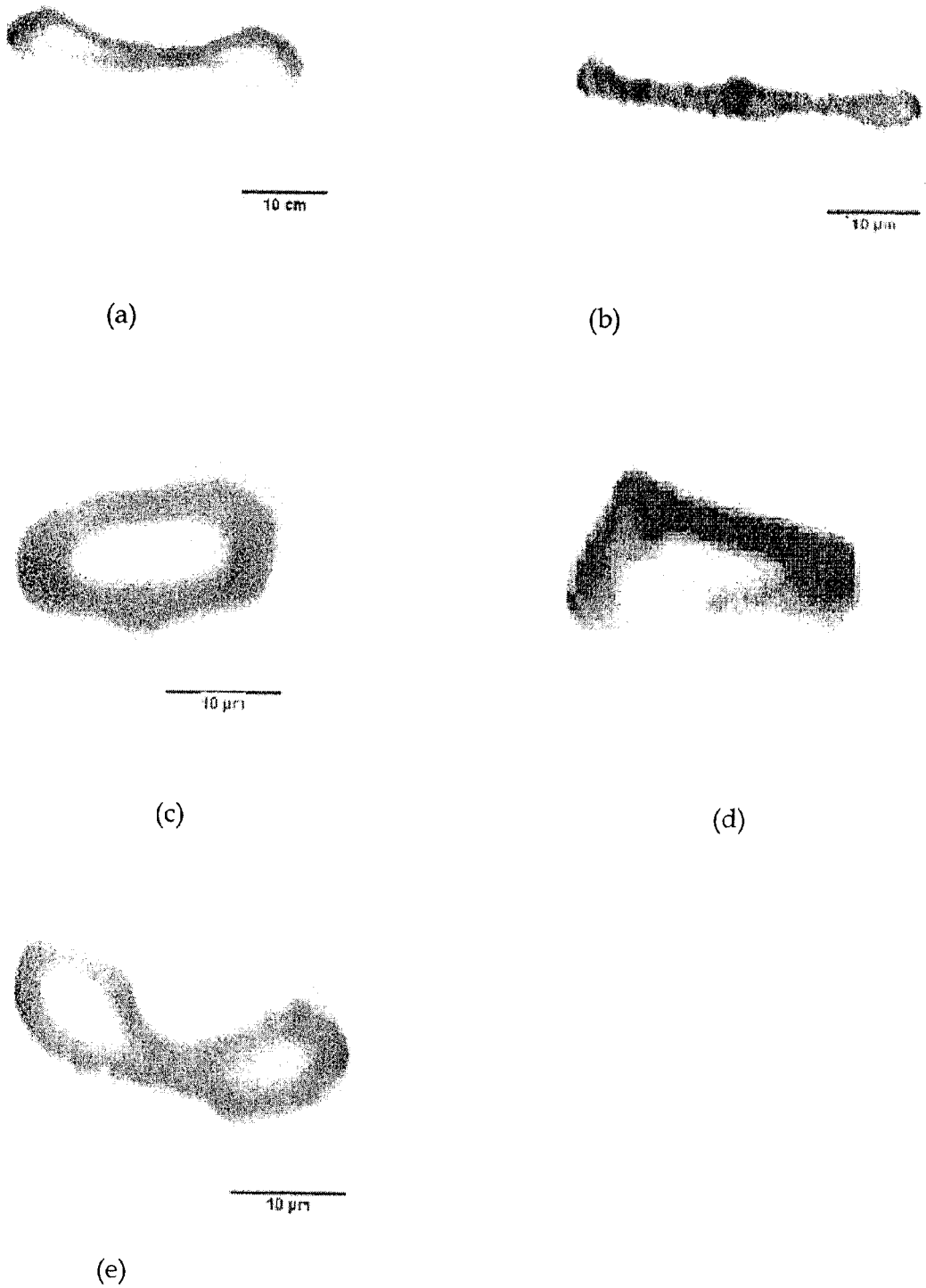
FIG. 16(a) is an optical section according to the invention of a Spruce BKP fibre taken in the YZ plane without wet pressing.
FIG. 16(b) is an optical section according to the invention of a Birch BCTMP fibre taken in the YZ plane without wet pressing.
FIG. 16(c) is an optical section according to the invention of a Birch BCTMP fibre taken in the YZ plane after wet pressing.
FIG. 16(d) is an optical section according to the invention of an Aspen BCTMP fibre taken in the YZ plane without wet pressing.
FIG. 16(e) is an optical section according to the invention of an Aspen BCTMP fibre taken in the YZ plane after wet pressing.
Figure 17:
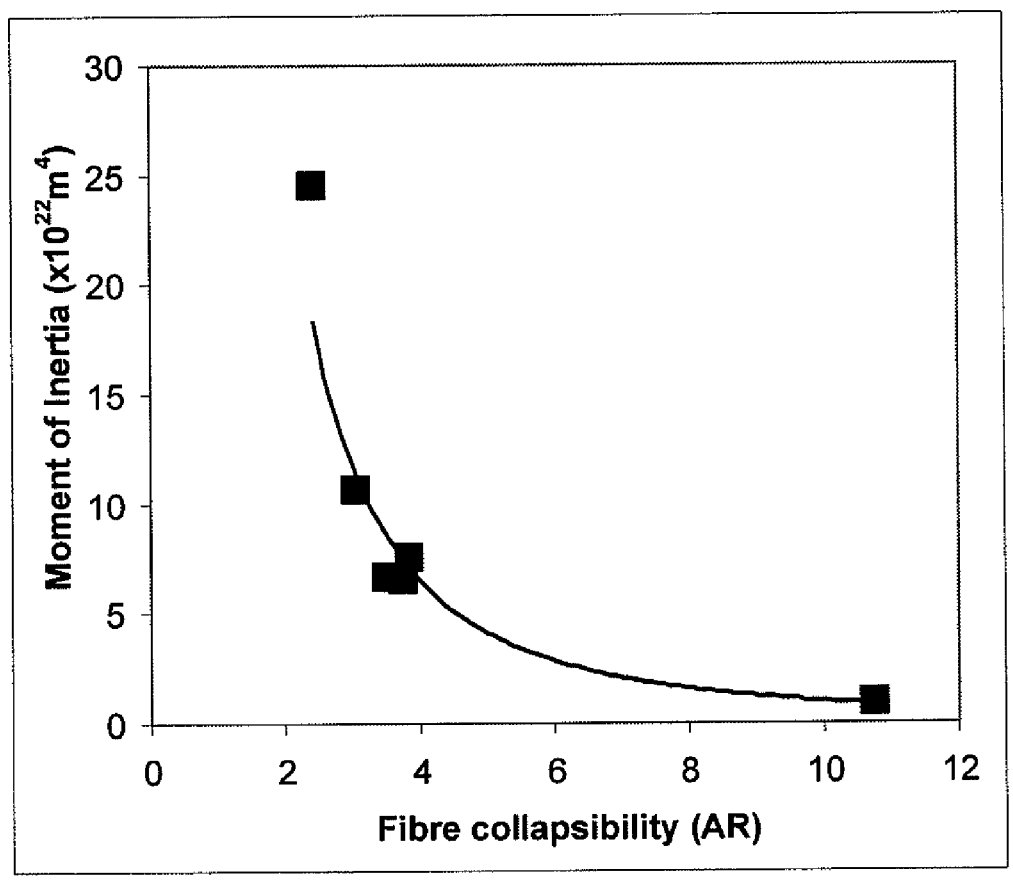
FIG. 17 is a graph according to the invention showing the effect of fibre collapsibility on fibre moment of inertia.
Figure 20:
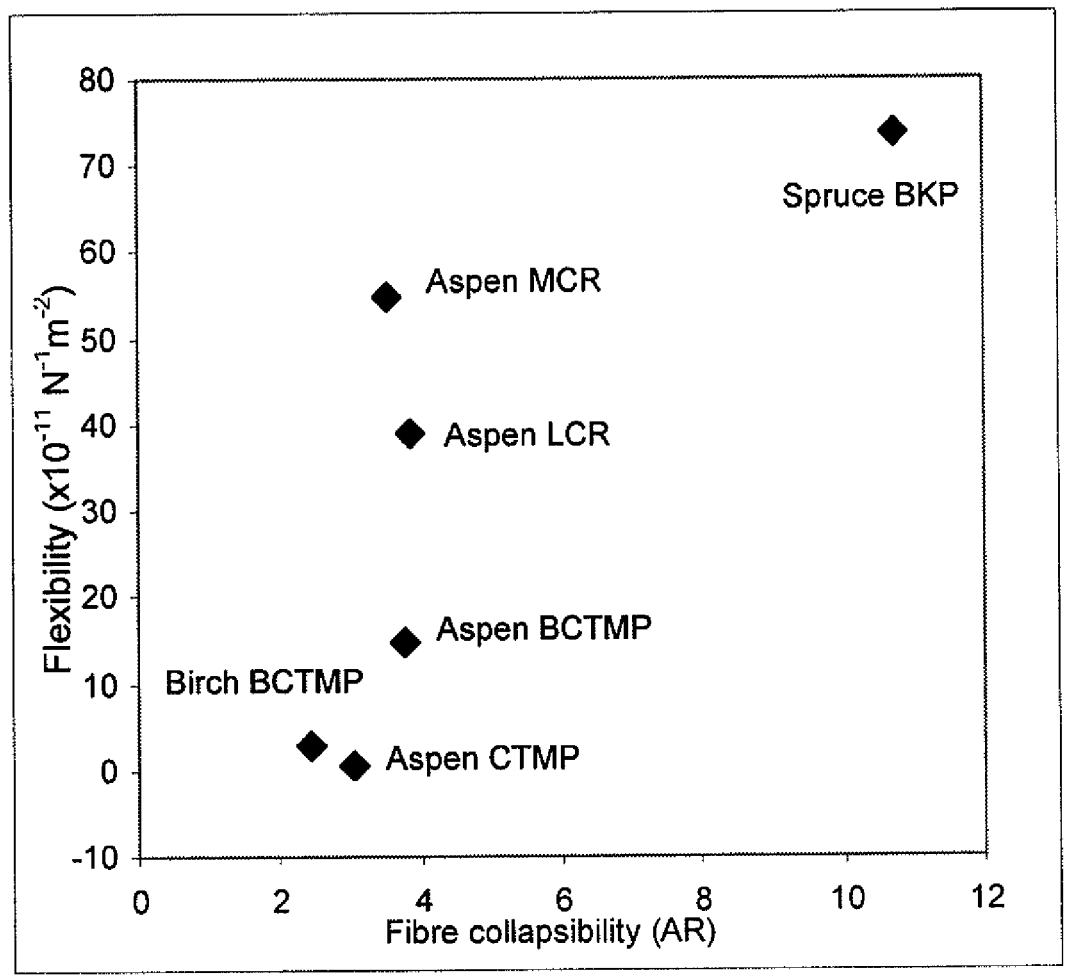
FIG. 20 is a graph according to the invention showing the relationship between measured fibre flexibility and collapsibility.
Figure 21:
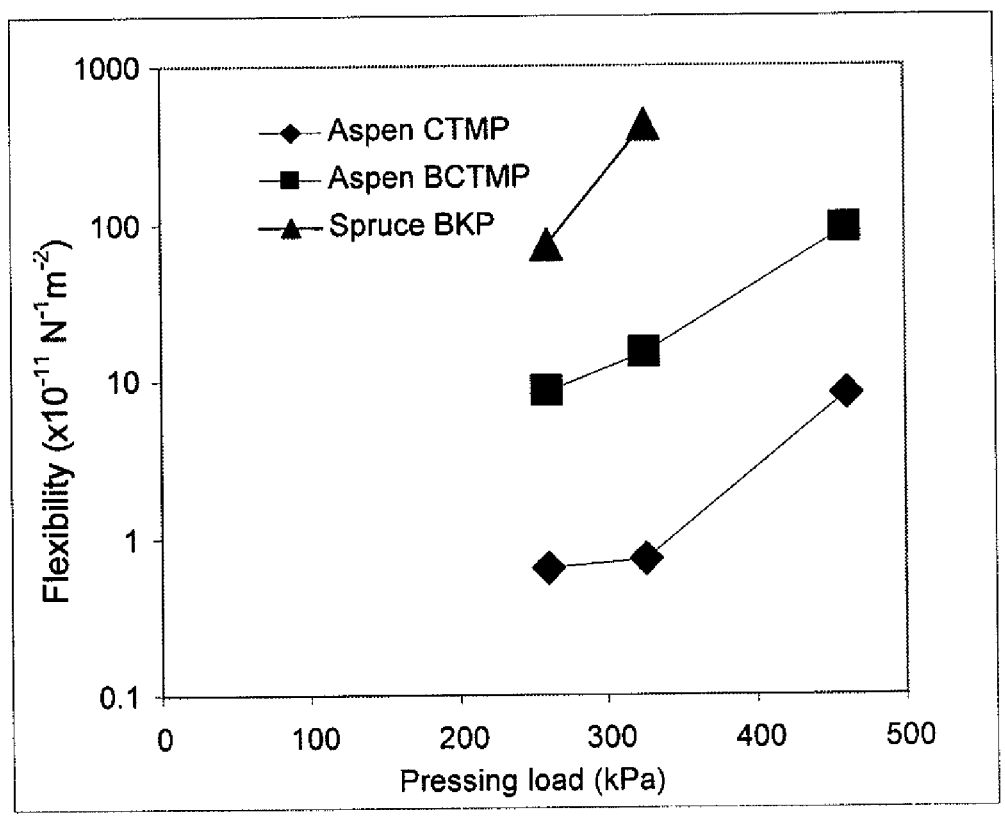
FIG. 21 is a graph according to the invention showing the effect of wet pressing on measured flexibility values.

Since CLSM can image the fibre cross-section directly, the collapsibility and the moment of inertia can be obtained when the fibre flexibility is measured. Therefore, additional information on how the fibre collapsibility affects the fibre flexibility can be revealed. FIG. 16 shows typical cross-section images of fibres obtained with CLSM. Thin-walled Spruce BKP fibres collapsed completely without wet pressing (FIG. 16a). The thick walled mechanical fibre (Birch BCTMP fibres) only collapse slightly after pressing (FIG. 16c) compared to before pressing (FIG. 16b). Aspen BCTMP fibres originally collapsed partially before wet pressing (FIG. 16d). After pressing, they collapsed almost completely (FIG. 16e). The aspect ratios (AR) listed in FIG. 24 give quantitative information of the collapsibility of the different types of fibres during flexibility measurement.

Once fibres collapse, the thickness of the fibre cross-sections reduce greatly, thus reducing the moment of inertia of the fibre. Therefore, the collapsibility of fibres affects the flexibility of the fibres through reducing the moment of inertia. FIG. 9 shows the relationship between fibre moment of inertia and the fibre collapsibility. When the fibre collapsibility is small, as for the BCTMP fibres, a small change of fibre collapsibility can cause significant change in fibre moment of inertia. It can also be seen in FIG. 24 that both bleaching and refining increased significantly the fibre collapsibility of Aspen fibres.

It can be seen from FIG. 16 that fibre collapsibility is essentially determined by the fibre wall thickness. Thin-walled BKP fibres collapse completely without any wet pressing. The thick-walled Birch fibres collapse only partially even after pressing. FIG. 16 illustrates how the fibre wall thickness affects the fibre collapsibility (AR) and, in turn, affects the fibre moment of inertia.

Fibre-Wall Modulus

With CLSM, the moment of inertia can be calculated with Equation 3. This makes it possible to measure the longitudinal elastic modulus of the fibre wall. It can be seen from FIG. 24 that the elastic modulus obtained in this study is within the range of 1.4 GPa-17.2 GPa for the softwood BKP and hardwood BCTMP. The result is comparable to the elastic modulus of wet pulp fibres obtained with micro-tensile test, which is on the order of 10 GPa [20, 23]. For Spruce BKP, the measured elastic modulus of 1.4 GPa is slightly lower than 4.3 GPa reported by Ehrnrooth [23] for Spruce kraft pulp fibres. In addition to the difference in the types of fibres, the contribution of shear deformation to measured flexibility may lead to a lower E calculated from Eq. 3 due to the pure bending assumption, according to Waterhouse and Page [20].

Both bleaching and refining altered the elastic modulus of the fibre wall significantly (FIG. 24). The elastic modulus of Aspen CTMP has been reduced from 17.2 GPa to 2.3 GPa by bleaching and is then further reduced to 0.7 GPa and 0.2 GPa by LC refining and MC refining, respectively. It is interesting to find that the elastic modulus does not much affect the fibre collapsibility. As shown in FIG. 24, different Aspen fibres have almost the same AR but completely different E, from 0.2 GPa to 17.2 GPa. This, on the other hand, further confirms that fibre wall thickness is the predominant factor in determining the fibre collapsibility.

In general, collapsed fibres are more flexible. For Aspen fibres, the flexibility is mainly determined by the elastic modulus, and the collapsibility has little effect since it does not change much. Bleaching and mechanical treatment altered slightly the collapsibility but improved significantly the flexibility. This new understanding may have significant impact on the use of BCTMP fibres in wood-free fibre paper grades and multi-ply board grades. In both cases, the major objective is to increase paper bulk by adding BCTMP fibres in the furnish. However, adding too much BCTMP may reduce the paper strength. Bleaching does not increase the fibre collapsibility, which means paper bulk can be maintained, but bleaching can increase fibre flexibility through decreasing the elastic modulus of the fibre wall, thus increasing the bonded area among fibres. Therefore, the manufacturer may adjust the pulp properties by modifying the bleaching process in BCTMP manufacturing.

The following references are referred to in this application and are incorporated herein by reference:

1. NILSSON, B., LARS WÅGBERG and GRAY, D., "Conformability of wet pulp fibres at small Length Scales". 12th Fundamental Research Symposium, p. 211 (2001)
2. JANG, H. F., "A theory for the transverse collapse of wood pulp fibres". 12th Fundamental Research Symposium p. 193 (2001)
3. SAMUELSSON, L. G., "Measurement of the stiffness of fibres". Svensk. Papperstidn 15(1):S41-S46 (1963)
4. MOHLIN, U-K., "Cellulose fibre bonding Part 5: Conformability of pulp fibres". Svensk. Papperstidn 78(11): 412-416 (1975)
5. KEREKES, R. J. and TAM DOO, P. A., "Wet fibre flexibility of some major softwood species pulped by various processes". J. Pulp Paper Sci. 11:60-61 (1985)
6. KUHN, D. C. S., LU, X., OLSON, J. A. and ROBERTSON, A. G., "Dynamic wet fibre flexibility measurement device". J. Pulp Paper Sci. 21(1):337 (1995)
7. STEADMAN, R. and LUNER, P., "The effect of wet fibre flexibility of sheet apparent density". 8th Fundamental Research Symposium p. 211 (1981)
8. SEBORG, C. O. and SIMMONDS, F. A., "Measurement of stiffness in bending of single fibres". Paper Trade Journal 113(1):49-50 (1941)
9. JAMES, W. L., "A method for studying the stiffness and internal friction of individual fibres. Wood Sci. 6(1):30-38 (1973)
10. TAM DOO, P. A. and KEREKES, R. J., "Method to measure wet fibre flexibility". Tappi 64:113-116 (1981)
11. ZHANG, M., HUBBE, M. A., VENDITTI, R. A. and HEITMANN, J. A., "Effects of sugar addition before drying on the wet flexibility of redispersed kraft fibres". J. Pulp Paper Sci. 30:29-34 (2004)
12. DELGADO, E., LOPEZ-DELLAMARY, F. A., ALLAN, G. G., ANDRADE, A., CONTRERAS, H., REGLA, H. and CRESSON, T., "Zwitterion modification of fibres: Effect of fibre flexibility on wet strength of paper". J. Pulp Paper Sci. 30:141-144 (2004)

13. KARNIS, A., "Mechanism of fibre development in mechanical pulping". J. Pulp Paper Sci. 20(1):280-288 (1994)
14. THE MATHWORKS INC., "Matlab Reference Manuel". (2004)
15. OTSU, N., "A threshold selection method from gray-level histograms". IEEE Transactions on Systems, Man and Cybernetics SMC-9:62-6 (1979)
16. HARALICK, R. M. and Linda, G. S., Computer and robot vision, Addison-Wesley, (1992)
17. JANG, H. F. and SETH, R. S., "Characterization of the collapse behaviour of papermaking fibres using confocal microscopy". In the proceedings of the 84th Annual Meeting of the Technical Section of Canadian Pulp and Paper Association, p. 205 (1998)
18. MARK, R. E., Handbook of Physical Testing of Paper II, Marcel Dekker, NY, (2002)
19. JANG, H. F., ROBERTSON, A. G. and SETH, R. S., "Measuring fibre coarseness and wall thickness distributions with confocal microscopy". In the proceedings of 78th Annual Meeting of the Canadian Pulp and Paper Association, Montreal, Quebec, Canada, p. 189 (1992)
20. WATERHOUSE, J. F. and PAGE, D. H., "The Contribution of Transverse Shear to Wet Fibre Deformation Behavior". Nordic Pulp and Paper Research Journal 19:89-92 (2004)
21. LAWRYSHYN, Y. A. and KUHN, D. C. S., "Large deflection analysis of wet fibre flexibility measurement techniques". J. Pulp Paper Sci. 22(1):423-431 (1996)
22. LOWE, R. RAGAUSKAS, A. and PAGE, D. H. "Imaging fibre deformations". In Advances in Paper Science and Technology, Proc. 13th Fundamental Research Symposium (S. J. I'Anson, ed.), pp. 921, FRC, Manchester, 2005.
23. EHRNROOTH, E. M. L. and KOLSETH, P., "The tensile testing of single wood pulp fibres in air and water". Wood Fibre Sci. 16(4):549-566 (1984)

We claim:

1. A method for measuring a property of a fibre comprising the steps of:
    (a) providing a fibre;
    (b) wetting the fibre;
    (c) deforming the fibre in its wet state around an object by applying a pressing load at a controlled pressure;
    (d) acquiring an optical section image by a CLSM of the deformed fibre;
    (e) making a measurement on the image; and
    (f) calculating the property using the measurement
    wherein the optical section image is a transverse image and the property is flexibility.

2. The method according to claim 1 further including the step of defining a neutral bending plane and a plane of the substrate on which the fibre is mounted.

3. The method according to claim 2 wherein the measurement is made with reference to the neutral bending plane and the plane of the substrate.

4. The method according to claim 3 wherein the measurement consists of measuring a freespan length and a deflection height.

5. The method according to claim 4 further including the step of quantifying the pressing load used in deforming the fibre and wherein the flexibility of the fibre is calculated according to the equation:

$$\text{flexibility} = 72d/qL^4$$

where d is the deflection height, L is the freespan length and q is the pressing load.

6. A method for measuring a property of a fibre comprising the steps of:
    (a) providing a fibre;
    (b) wetting the fibre;
    (c) deforming the fibre in its wet state around an object by applying a pressing load at a controlled pressure;
    (d) acquiring an optical section image by a CLSM of the deformed fibre;
    (e) making a measurement on the image; and
    (f) calculating the property using the measurement
    and further including the step of defining a neutral bending plane,
    wherein the optical section image is a cross-section and the property is fibre collapsibility.

7. The method according to claim 6 wherein the measurement is made with reference to the neutral bending plane.

8. The method according to claim 7 wherein the measurement consists of measuring fibre thickness and fibre width.

9. The method according to claim 8 wherein the fibre collapsibility is measured according to the following equation:

$$AR = \frac{D_{min}}{D_{max}}$$

where $D_{min}$ is the shortest Feret diameter as measured on the image and $D_{max}$ is the longest Feret diameter as measured on the image.

10. A method for measuring a property of a fibre comprising the steps of:
    (a) providing a fibre;
    (b) wetting the fibre;
    (c) deforming the fibre in its wet state around an object by applying a pressing load at a controlled pressure;
    (d) acquiring an optical section image by a CLSM of the deformed fibre;
    (e) making a measurement on the image; and
    (f) calculating the property using the measurement
    wherein the optical section image is a cross-section and the property is the fibres moment of inertia and,
    wherein the image is a binarized image and further including the step of defining a neutral bending plane on the image.

* * * * *